United States Patent [19]

Förster

[11] Patent Number: 5,509,320
[45] Date of Patent: Apr. 23, 1996

[54] METHOD AND APPARATUS FOR TESTING ELONGATED OBJECTS HAVING A NON-CIRCULAR CROSS-SECTION

[75] Inventor: Friedrich M. Förster, Pfullingen, Germany

[73] Assignee: Institut Dr. Friedrich Forster, Reutingen, Germany

[21] Appl. No.: 279,288

[22] Filed: Jul. 22, 1994

[30] Foreign Application Priority Data

Aug. 26, 1993 [DE] Germany ............................ 43 28 711.5

[51] Int. Cl.⁶ ..................... G01B 2/30; G01B 7/34; G01N 27/90; B21C 51/00
[52] U.S. Cl. ........................ 73/866.5; 324/237; 324/238; 324/240
[58] Field of Search ..................... 73/866, 866.5, 73/621, 622, 865.9; 324/237, 238, 240

[56] References Cited

U.S. PATENT DOCUMENTS

| | | | |
|---|---|---|---|
| 3,169,393 | 2/1965 | Stebbins | 73/622 |
| 3,731,184 | 5/1973 | Goldberg et al. | |
| 3,777,552 | 12/1973 | Fletcher et al. | 73/622 |
| 4,596,953 | 6/1986 | Nagasaka et al. | 73/622 |
| 4,599,900 | 7/1986 | Friedman | 73/622 |
| 4,641,092 | 2/1987 | Sakamoto et al. | 324/237 |
| 4,644,274 | 2/1987 | Casarcia | 324/237 |
| 4,679,437 | 7/1987 | Koike et al. | 73/622 |
| 4,767,986 | 8/1988 | Tornblom | 324/237 |
| 4,864,239 | 9/1989 | Casarcia et al. | 324/237 |
| 4,906,927 | 3/1990 | Urata et al. | 324/238 |
| 5,007,291 | 4/1991 | Walters et al. | 73/622 |
| 5,041,786 | 8/1991 | Takaishi et al. | 324/237 |
| 5,311,785 | 5/1994 | Bar-Shay | 73/866.5 |
| 5,313,837 | 5/1994 | Haynes | 73/622 |

FOREIGN PATENT DOCUMENTS

| | | | |
|---|---|---|---|
| 2637283 | 2/1977 | Germany | 73/621 |
| 3527972 | 3/1985 | Germany . | |
| 3802072 | 1/1988 | Germany . | |
| 63-11853 | 2/1989 | Japan . | |
| 63-271157 | 2/1989 | Japan . | |

*Primary Examiner*—Richard Chilcot
*Assistant Examiner*—George M. Dombroske
*Attorney, Agent, or Firm*—Bell, Seltzer, Park & Gibson

[57] ABSTRACT

A test head through which passes a test object has at least one test probe guided in a circular orbital path around the test object. The shape of the circular orbital path of the probe, when considered in the travel direction of the object, diverges in a predetermined manner from a circular shape. A rotor guides the probe on a circular path, and the rotational axis of the rotor can be tilted with respect to the travel direction of the test object. The rotor is driven by a driving unit positioned laterally to the travel direction on a base plate by a belt drive which runs in a transmission element carrying the test head and linking it with a drive unit.

10 Claims, 3 Drawing Sheets

METHOD AND APPARATUS FOR TESTING ELONGATED OBJECTS HAVING A NON-CIRCULAR CROSS-SECTION

BACKGROUND OF THE INVENTION

The invention relates to a method for testing elongated objects having a non-circular cross-section by at least one test probe guided over a circular path or orbit around the object, as well as a testing apparatus for performing the method with a test head traversed by the object and which is provided with at least one test probe, which is guided on a circular path or orbit surrounding the object. The invention more particularly relates to the problem of continuously, uninterruptedly and non-destructively testing for surface defects, preferably directly after their manufacture, metallic semifinished products having a non-circular cross-section. Particular interest is attached to e.g. spring wires having an elliptical or oval cross-section, such as are used to an increasing extent in the construction of valve springs in car engine building.

PRIOR ART

The testing for surface defects within the framework of the quality control of metallic semifinished products such as wires, rods or tubes are at present frequently performed on the basis of an eddy current procedure. A known apparatus of this type for the testing of objects having a circular cross-section has a test head, which can be installed in the production line of a semifinished product in such a way that the object being tested passes through the central axis of the test head. Within the test head rotate test probes, constructed as eddy current probes, fitted to a rotor in a plane perpendicular to the longitudinal axis of the object being tested, at high speed around the longitudinally moved test object, whereby high frequency eddy currents are induced, whose induced magnetic fields are recorded again by the test probes as a measuring signal. Surface defects of the test objects, which are located on the helical scanning paths of the test probes give rise to interference to the eddy currents and therefore to changes in the measuring signal.

For an uninterrupted surface testing it is necessary to match to one another the speed, number and track width of the test probes, as well as the test material running speed. Thus, e.g. with four test probes and speeds of 9000 r.p.m., testing speeds in the axial direction of up to 3 m/s are possible.

Like surface defects, divergences of the test part cross-sections from the circular shape due to the modified spacing between the test part surface and the probe give rise to measuring signals which, if the spacing change does not exceed a certain amount, can be compensated by an electronic spacing compensation and consequently do not lead to an erroneous indication of surface defects, However, large diameter differences of the test part cross-section, such as can typically occur in the case of wires having an elliptical or oval cross-section, cannot be adequately electronically compensated, or this can only take place with great technical expenditure and therefore uneconomically.

Eddy current passage coils, in which both circular and profiled test parts are guided through fixed difference or absolute test coils, have a simple construction and high test speeds. They constitute cost-effective testing possibilities with respect to hole, transverse and longitudinal defects, but have a limited resolution for small defects and do not provide adequate test results for relatively thin wires, such as are e.g. required for valve spring construction.

SUMMARY OF THE INVENTION

The problem of the invention is to provide a method making it possible to test elongated objects, particularly wires, having a non-circular cross-section, as well as to an apparatus for performing such a test.

The solution for this problem is achieved in accordance with the present invention by the provision of a method and apparatus which are particularly suitable for performing the testing of such objects whilst maintaining the aforementioned advantages attainable through the use of rotary technology, such as high testing speeds and at the same time high resolution.

According to the invention a test probe, particularly a magnetic probe, is guided around an object to be tested on a probe orbit, whose shape can diverge in the object travel direction from a circular shape. If the travel direction projection of the orbit of the test probe is adapted to the shape of the cross-section of the object to be tested, then the interaction between the test probe and the test object can be utilized in a particularly simple manner for material testing purposes. Particularly for testing objects having an elliptical cross-section, an embodiment is particularly advantageous in which the test probe is guided on a circular path, whose plane is set at a setting angle diverging from 90° with respect to the test object travel direction. On its circular orbit a constant centripetal force applied by its suspension acts on the test probe in the case of a constant peripheral speed and with an appropriate design of the suspension, e.g. by a mass compensation, allows very high probe rotation speeds with minimum loading of the bearings.

A high path speed of the test probe on its orbit is permitted in the case of longitudinally moved test objects and probes acting in "punctiform" manner, where for test method resolution reasons at any time only a very small area of the material surface is to be detected, permits a complete and high resolution scanning of the entire material surface and at the same time a high test object travel speed. With an elliptical travel direction projection of the test probe orbit produced by a setting angle diverging from 90°, the ratio of the radius of the ellipse is substantially determined by the magnitude of the setting angle. For testing test parts with different diameter ratios it is consequently advantageous for the probe orbit to be tiltable with respect to the test object travel direction. If the probe orbit can be modified, e.g. by radial displaceability of the probes, then the testing apparatus can easily be adapted to test objects having the most varied cross-sectional shapes and sizes.

A rotary probe in which the centre of its circular orbit is located on the longitudinal axis of the test object, but where the orbit plane is not perpendicular to said longitudinal axis, during its rotation periodically changes its relative orientation to the in each case facing radius vectors of the test object, the radial directions of the test object, considered from the probe, are in a solid angle range, whose sector angle corresponds to twice the amount of the divergence of the setting angle from 90°. With such an arrangement the further processing of the test signal is particularly simple if the testing sensitivity of the probe, at least over said sector, is substantially constant. At all setting angles where the test object radii are in the angular range of constant testing sensitivity, it is possible then to carry out tests without significant changes to the electronic settings of the measuring apparatus. Small divergences of the test object cross-section from the elliptical shape can be advantageously compensated by an electronic signal compensation, in which e.g. the radial spacing between the object surface and the probe is determined and divergences from the desired value are utilized for a signal correction. As a result of the shape of the test probes and their axial extension, there is an effective passage cross-section, which could diverge from the ideal elliptical shape and e.g. be lenticular. Thus, with setting angles differing only slightly from 90° larger radius differences could occur than would result from "punctiform" acting probes due to the elliptical orbit.

For a given testing sensitivity, which is not constant over the testing sector, or with non-ideally "punctiform" acting probes, there would be a periodically varying measuring signal. It would be conceivable, optionally following a calibration of the apparatus electronically, to only use divergences from said periodically varying signal for the detection of surface defects. A differential signal between a measuring point on the test object and a reference point with the same cross-section and same material, such as could be achieved by an appropriate series connection of two identical probe orbits, could be used for the detection of surface defects.

The handling of the testing apparatus, particularly during inspection, cleaning and retooling processes, and the adaption thereof to the devices guiding the test objects, such as e.g. wire drawing machines, can be advantageously facilitated in that the drive unit for the test head is positioned laterally with respect to the passage path of the objects. The test head can be connected by means of a transmission or transfer element to the drive unit. The transmission element can be an arm acting on the drive unit and test head, which has a belt drive for transmitting to said head the rotary movement produced by the drive unit and optionally incorporates the same. Such a design with a spatial separation of drive unit and test head combines a number of advantages. The test head can be made very compact, i.e. in particular light and short in the test object travel direction. Therefore it can be positioned around the test object passage path with a minimum of necessary adjustments, because the test head axis and the object passage path need not be parallel. For long test heads divergences from the parallelism of the passage path and test head axis could easily lead to undesired contacts between the testing apparatus and the test object, so that an accurate adjustment is necessary. Moreover, the test head located on the transmission element could easily be brought by means of a pivoting about the belt drive axis of the drive element out of the test object passage path into a service position, where it would be possible to carry out e.g. retooling activities, as well as cleaning and inspections on the test head.

By means of the setting of the pivoting position of the transmission element, it is also possible to easily set the height position of the test head around the test object. If the drive element preferably constructed as a three-phase motor is fixed e.g. with electronic elements of the testing apparatus on a base plate, which can be mounted on vibration mounts, then a lateral correction of the orientation of the test head around the test object could take place by movements of the testing apparatus in the base plate bearings about an axis perpendicular to the base plate, so that a type of automatic lateral centering of the testing apparatus can be brought about by the test object. The use of difficult to handle and expensive lifting/sliding tables for test head centering would be rendered superfluous by such a construction.

The positioning of the test head is particularly advantageous for test condition constancy reasons where minimum lateral movements are superimposed on the longitudinal movement of the test object. Therefore the test head can be advantageously positioned following a guiding device for the test object and in the case of wire drawing machines this can be directly behind the draw plate hole.

The advantages of test probes rapidly revolving on circular paths could be used for test objects with cross-sections diverging from the elliptical, particularly for those whose cross-sectional circumference can be formed from circular or elliptical segments. Thus, for valve spring wire cross-sections the particularly advantageous oval shape is approximately formed from a circular segment and an elliptical segment. A series connection of a test probe rotating in circular manner in the travel direction of the test object and a test probe rotating on an elliptical path in said test object passage direction with suitable reversals between the two test signals on the imaginary intersections of the elliptical and circular paths could be utilized for testing such a wire geometry. In the same way with two elliptical orbit projections reciprocately displaced by 90° about the passage direction a substantially square test object could be covered, the curvatures of the resulting lateral face segments decreasing with increasing divergence of the setting angle from 90°. It would also be possible to test objects having a lenticular cross-section, if two elliptical passage projections with identical or different radius ratios, are reciprocately displaced e.g. in the direction of the short radius of the ellipse.

The term test probe can be used to cover all devices which are employed for recording or producing and recording spatial distributions of physical parameters and which can be brought into a spatial relationship with the test object, such as e.g. eddy current probes or magnetic stray flux probes. However, probes operating on optical or acoustic principles are also possible.

These and other features and constructions of the invention can be gathered from the claims, description and drawings and the individual features, both singly and in the form of subcombinations, can be realized in an embodiment of the invention and in other fields and represent advantageous, independently protectable constructions for which protection is hereby claimed. Embodiments of the invention are described in greater detail hereinafter relative to the drawings.

DESCRIPTION OF THE EMBODIMENTS

Figure 1:
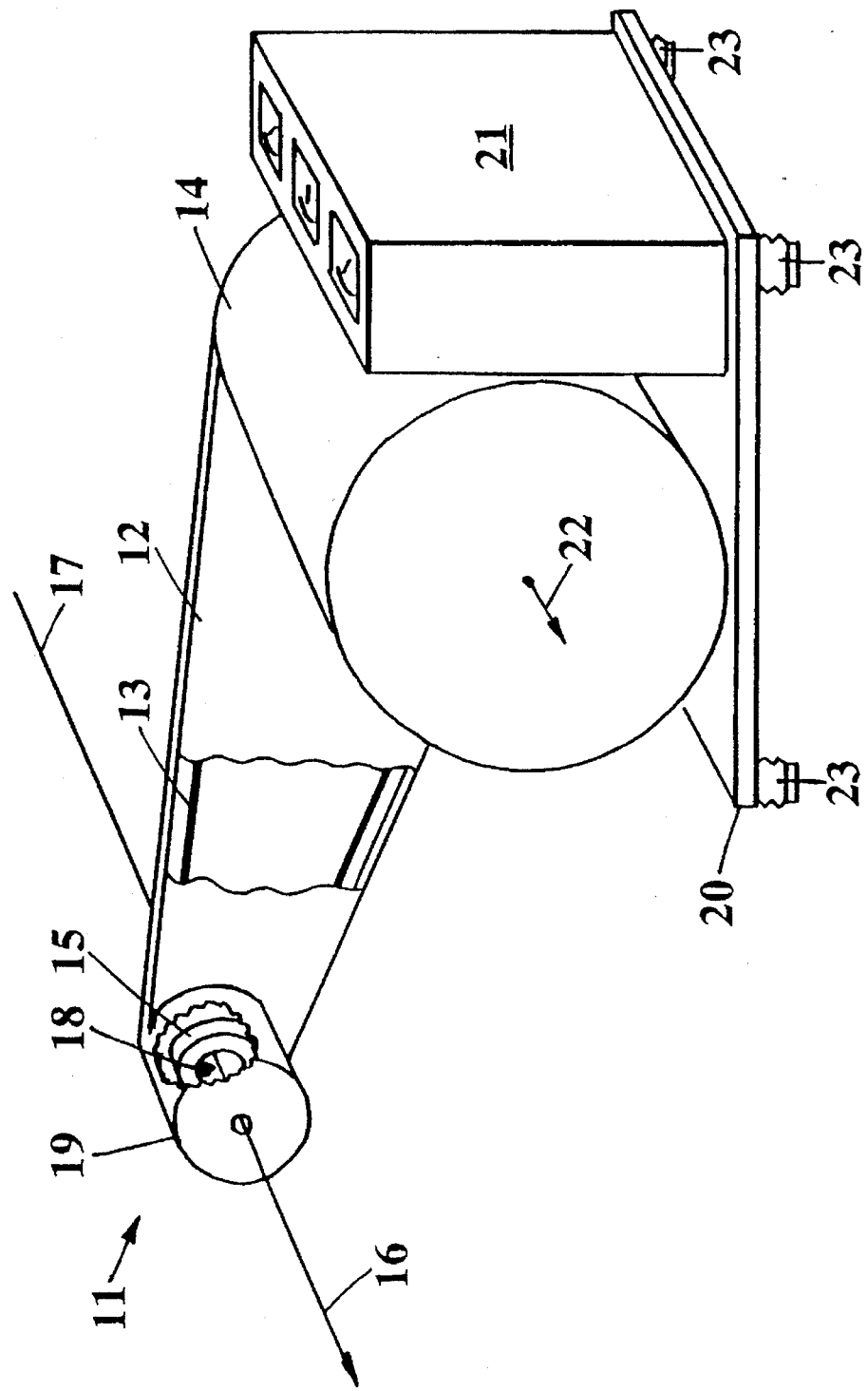
FIG. 1 is an overall view with partial section of an embodiment of the testing apparatus.

In the case of the preferred embodiment of the testing apparatus shown in FIG. 1 a test head 11 is located on a transfer or transmission element 12, which incorporates a belt drive 13, which by means of not shown transfer or transmission means transfers or transmits the rotary movement produced by a drive unit 14 to the rotor 15 of the test head 11. On the rotor 15, whose rotation axis can be tilted with respect to the travel direction 16 of a test object 17 indicated by the arrow, is placed a test probe 18, which on rotating the rotor 15 is guided on a circular orbit or path around the test object 17, which in FIG. 1 is a thin wire.

In the represented embodiment the rotor 15 has a single test probe 18 and a mass compensation on the rotor 15 can ensure a bearing-protecting concentricity of the rotor. There can also be two diametrically facing test probes or several, in particular four, probes distributed symmetrically around the rotor circumference.

As a result of the represented construction of the test head 11 with a rotor 15 rotating within a stator casing 19, by increasing the speed of the test probes the already high throughput of the head can be increased in a simple manner. The diameter of the circular path or orbit of the test probe 18 can e.g. be continuously adjustable by a rotary spiral disk, so that the testing apparatus can easily be adapted to test objects having different dimensions. As a result of its construction the mechanism of this very efficient and variable test head can be completely implemented with easily and accurately manufacturable turned parts.

The connection of the test probe 18, which in the represented embodiment is an eddy current probe, with preamplifiers and power drivers placed alongside the drive unit 14 on a base plate 20 and which are surrounded by a casing 21 can be created e.g. by a contactless and wear-free functioning rotary transmission means for field, measurement and optionally spacing channels located on the back of the test probes. One spacing channel is part of an electronic signal compensation, which permits an exact reception and interpretation of a test signal even if the cross-sections of the test objects differ somewhat from the precise elliptical shape, i.e. if during a rotation of the probes about the test object the spacing between the probe and the object surface and therefore also the spacing-caused testing sensitivity of the probe undergoes a slight local variation.

In the embodiment shown in FIG. 1 an exact placing of the test head 11 around the test object 17 is obtained, on the basis of its height, by pivoting the transmission element 12 carrying the head 11 about the pivoting axis 22 of the drive unit 14. A lateral correction is brought about by rotating the entire testing apparatus about an axis perpendicular to the base plate 20 and tilting corrections by an appropriate vertical adjustment of the feet 23 carrying the base plate 20 on which the latter is mounted in vibration mounts. As a result of this bearing minor lateral corrections can be brought about during the testing process by the actual test object in the manner of an automatic lateral centering.

Figure 2:
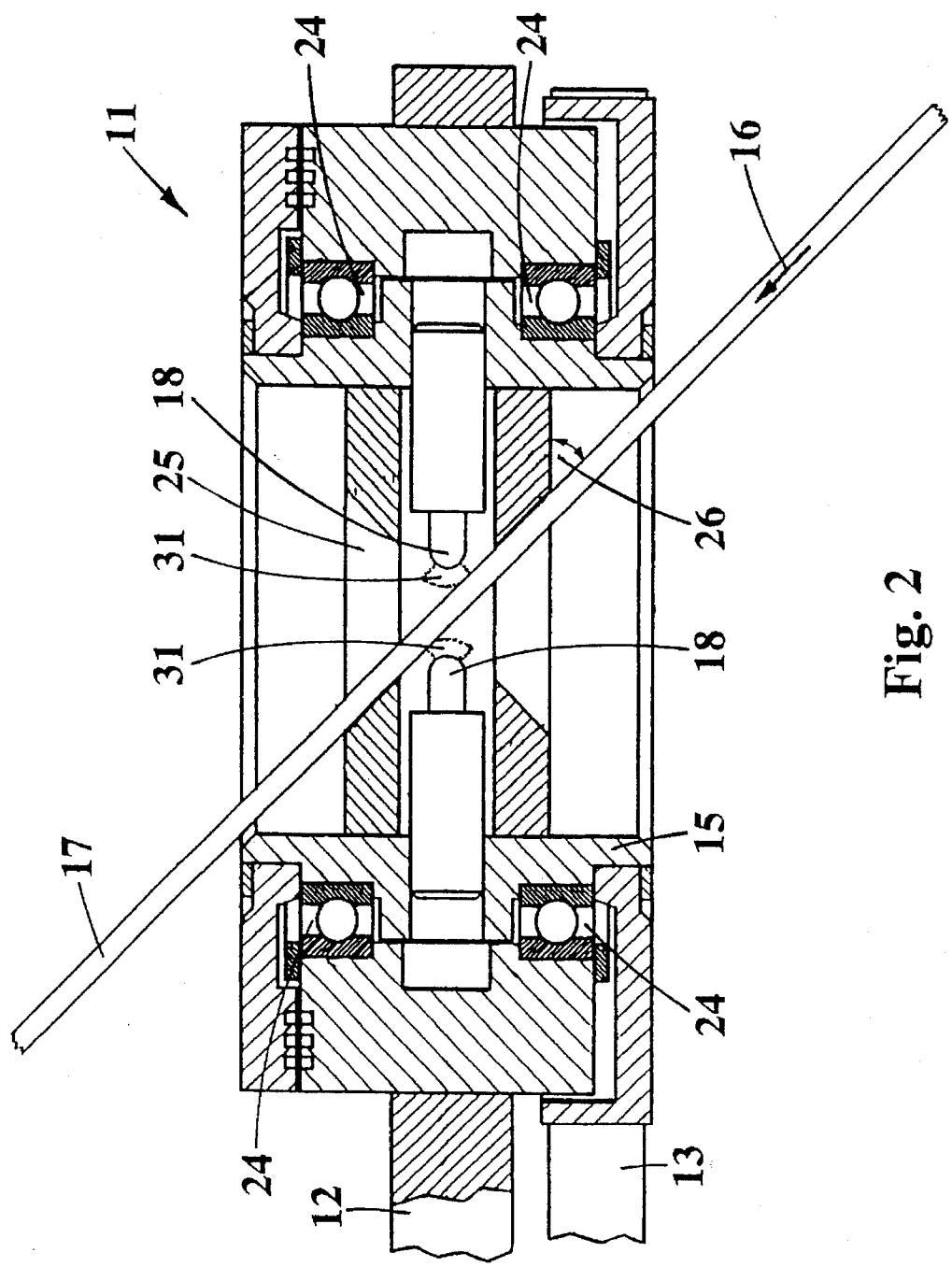
FIG. 2 is a section through the test head in plan view.

FIG. 2 is a diagrammatic section through another embodiment of a test head, in which two test probes 18 diametrically face one another on a rotor 15 guided by bearings 24. The rotor 15 is located in a stator 19, which has recesses 25, through which, in a travel direction 16 diverging from the rotor axis, a test object 17 is guided through the test head 11, so that the probes are guided around the object 17 on a circular probe orbit, which is set at an angle 26 differing from 90° with respect to the travel direction 16. It is possible to see the sector 31 over which the sensitivity of the test probes 18 is appropriately constant. The rotor 15 is drivable by a belt drive 13 guided by the transmission element 12.

FUNCTION

Figure 3:
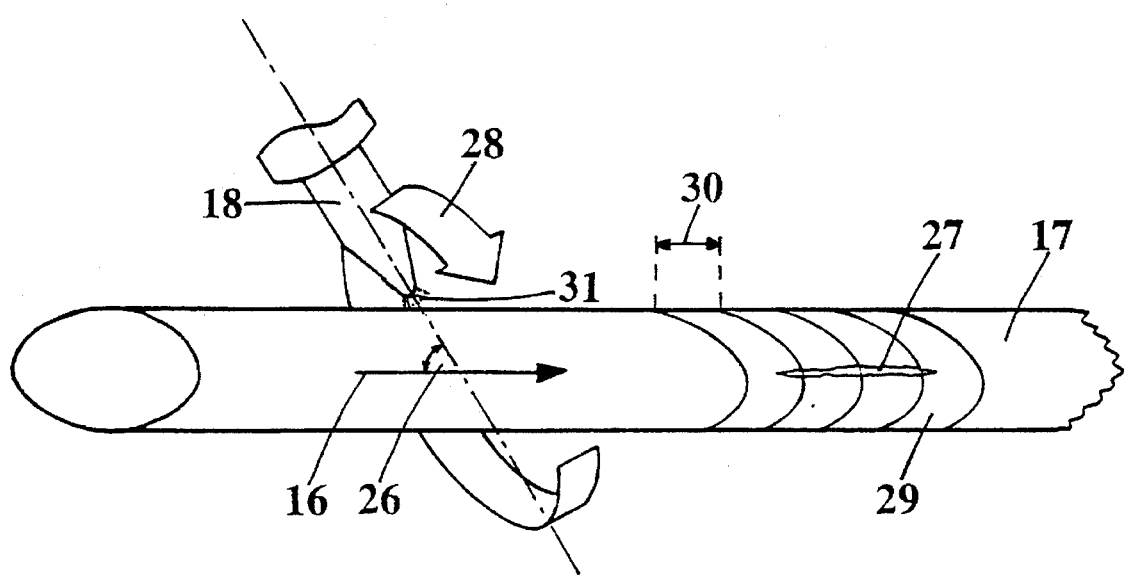
FIG. 3 is a diagrammatic drawing of the testing principle.

The testing method is explained with respect to FIG. 3, which shows the test object 17 as a wire, which has a longitudinal crack 27 and an elliptical cross-section (indicated to the left), which is moved in the travel direction 16 indicated by the arrow. By a suitable mounting of the rotor 15 and a suitable design of the components transmitting the belt drive movement or by the arrangement of the test head in accordance with FIG. 2, the plane containing the arc arrow of the probe orbit 28 is set at an angle 26 differing from 90° with respect to the travel direction 16. Thus, the circular probe orbit 28, considered in the travel direction 16, is elliptical.

The test probe 18 is preferably constructed as an eddy current probe, which at each point of its orbit has the same testing sensitivity in the radial direction of the wire 17. The sector 31 having an approximately constant testing sensitivity is visible. The probe acts in "punctiform" manner, i.e. the area of the surface of the test object from which the used test signals pass to the probe, is small, e.g. 5 mm in diameter. Through the circular movement of the probe 18 on its orbit 28 on the one hand and the movement of the wire 17 in the travel direction 16 on the other, the probe, without contacting the wire, scans the wire surface on a helical scanning path 29 around the wire, whereof the four uninterruptedly adjacent path segments tangent to the longitudinal crack 27 are shown. For an uninterrupted scanning of the entire test object surface in the case of a single test probe the travel speed of the test object is chosen in such a way that during a rotation of the probe said object is advanced by the amount of the testing width 30 of the scanning path 29. Thus, e.g. with a single probe having a testing width of 5 mm, in the case of a rotor speed of 36,000 r.p.m., an uninterrupted testing of an object travelling at 3 m/s is possible. When there are two diametrically facing probes, the travel speed of the test object 17 can be twice as high, because the probes 18 scan two scanning paths 29 with twice the gradient which are reciprocately displaced in the travel direction by a scanning width 30. When there are four probes and the rotor rotation speed is unchanged, then the test object can be uninterruptedly scanned when its travel speed is four times higher.

The resolution of the testing method is essentially determined by the size of the probe action area on the test object, i.e. from the area to whose signals the probes reacts. In the case of "punctiform" acting probes with a very small action area, a small defect, such as a crack, leads to a high percentage interference in the small probe action area and consequently produces a clear and readily interpretable test signal. Thus, e.g. with eddy current probes, a crack, i.e. an area where material is missing in the probe action area acts towards reduced electrical conductivity of the material tested by the probe.

It is particularly easy to analyse the test signals produced by the probe if the probe testing sensitivity does not change during its rotation around the test object. This is achieved in the examples of FIGS. 2 and 3 by a probe directional characteristic with a solid angle range 31 of constant testing sensitivity arranged symmetrically around the probe longitudinal axis and whose opening angle is at least twice the amount of the divergence of the setting angle 26 from 90°. Testing can be performed in a particularly reliable and low-error manner, if the test object is guided by the test head 11 with little or no divergence from the rotation axis of the rotor. This can be brought about by placing the test head following guidance means for the test object, because there the said object moves in a particularly quiet manner. In the case of wire testing, it is particularly advantageous to place the test head following a draw plate hole shaping the wire. The test probe can be protected from damage, i.e. contact with the test object by means of protective nozzles, which are positioned in front of the test probe in the test object travel direction.

I claim:

1. A method for testing an elongated object having a non-circular cross section and comprising the steps of advancing the elongated object along a travel direction and through a rotating rotor which defines a rotational axis and which mounts at least one test probe, adjustably positioning the rotor so that its rotational axis is inclined with respect to the travel direction of the advancing elongated object and so that when considered in the travel direction, the test probe is guided in a probe orbit which diverges in a predetermined manner from a circular shape.

2. The method as defined in claim 1 wherein the elongated object has an elliptical cross-section, and wherein the position of the rotor is selected so that when considered in the travel direction of the advancing elongated object, the test probe is guided in a probe orbit which is elliptical and generally conforms to the elliptical cross-section of the elongated object.

3. The method as defined in 1 wherein the test probe generates an electric output signal, and comprising the further step of electronically adjusting the output signal to compensate for small divergencies in the radial spacing between the surface of the elongated object and the orbiting test probe.

4. An apparatus for testing an elongated object having a non-circular cross-section and comprising a rotor mounting at least One test probe and being configured to permit an elongate object to be passed along a travel direction through the rotor, means mounting said rotor for rotation about a rotational axis which is adjustable so that it may be inclined with respect to the travel direction and so that when considered in the travel direction, the test probe is guided in a probe orbit which diverges in a predetermined manner from a circular shape, and means for rotating the rotor about its rotational axis.

5. The apparatus as defined in claim 4 further comprising an electronic signal compensation means connected to the output signal of said test probe for compensating for small divergences in the radial spacing between the object surface and the probe.

6. The apparatus as defined in claim 4, wherein the rotor mounting means mounts the rotor so that the one test probe is guided on a circular probe orbit, and the probe orbit defines a plane, and the plane may be set with respect to the travel direction at a setting angle which diverges from 90°.

7. The apparatus as defined in claim 6, wherein the one test probe has a directional characteristic and a testing sensitivity, whereby the directional characteristic is such that the testing sensitivity is substantially constant over a sector, the sector angle determining said sector being at least equal to twice the amount of the divergence of the setting angle from 90°.

8. The apparatus as defined in claim 4, wherein said rotor rotating means includes a test head which rotatably mounts said rotor, and a drive unit connected to the test head and positioned laterally from the test head with respect to the travel direction of the test object.

9. The apparatus as defined in claim 8, wherein an arm is interconnected between said drive unit and said test head, and a transmission element is located in said arm and rotatably interconnects said drive unit and said test head.

10. The apparatus as defined in claim 4, wherein the one test probe is an eddy current probe.

* * * * *